United States Patent [19]

Gassen et al.

[11] Patent Number: 5,081,283
[45] Date of Patent: Jan. 14, 1992

[54] FLUOROCYCLOPROPYL DERIVATIVE FUNGICIDE INTERMEDIATES

[75] Inventors: Karl-Rudolf Gassen, Odenthal; Bernd Baasner, Leverkusen, both of Fed. Rep. of Germany

[73] Assignee: Bayer Aktiengesellschaft, Leverkusen, Fed. Rep. of Germany

[21] Appl. No.: 692,824

[22] Filed: Apr. 26, 1991

Related U.S. Application Data

[63] Continuation of Ser. No. 374,201, Jun. 30, 1989, abandoned.

[30] Foreign Application Priority Data

Jul. 19, 1988 [DE] Fed. Rep. of Germany ....... 3824433

[51] Int. Cl.$^5$ .............................................. C07C 69/74
[52] U.S. Cl. .................................. 560/124; 560/18; 560/35; 560/65; 560/101; 560/102; 562/405; 562/432; 562/440; 562/474; 562/491; 562/492; 562/506; 568/43; 568/52; 568/55; 568/303; 568/325; 568/425; 568/442; 568/647; 568/700; 568/807
[58] Field of Search .................. 562/506; 560/124

[56] References Cited

U.S. PATENT DOCUMENTS

| | | | |
|---|---|---|---|
| 3,462,453 | 8/1969 | Popoff | 562/506 |
| 3,856,976 | 12/1974 | Hunter | 560/124 |
| 4,705,788 | 11/1987 | Schriewer | 514/254 |
| 4,871,852 | 10/1989 | Hayakawa | 544/363 |

FOREIGN PATENT DOCUMENTS 2653189  6/1977  Fed. Rep. of Germany .

OTHER PUBLICATIONS

JP 59-222430 A, "Fluorocyclopropane Derivative", Abstract of Japan, vol. 9, No. 91, Apr. 1985 (Shionogi Seiyaku).

*Primary Examiner*—Michael L. Shippen
*Attorney, Agent, or Firm*—Sprung, Horn, Kramer & Woods

[57] ABSTRACT

Novel intermediates for fungicides, comprising fluorocyclopropyl derivatives of the formula

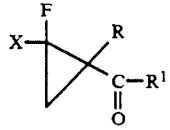

in which
R represents alkyl, optionally substituted aryl or optionally substituted aralkyl,
X represents hydrogen, chlorine or bromine and
$R^1$ represents hydroxyl, alkoxy, alkyl or halogen.

5 Claims, No Drawings

FLUOROCYCLOPROPYL DERIVATIVE FUNGICIDE INTERMEDIATES

This application is a continuation of application Ser. No. 374,201, filed Jan. 30, 1989, now abandoned.

The present invention relates to novel fluorocyclopropyl derivatives, several processes for the preparation thereof and their use as intermediates for the synthesis of compounds having fungicidal activity.

Certain cyclopropyl derivatives and their use as intermediates for the preparation of azolyl derivatives having fungicidal properties have already been disclosed (cf. EP-OS (European Published Specification) 0,040,345 and EP-OS (European Published Specification) 0,180,136). Thus, 1-(4-chlorophenoxy)-2-cyclopropyl-3-(1,2,4-triazol-1-yl)-propan-2-ol and 1-(4-chlorophenyl)-1-(1-chloro-cycloprop-1-yl)-2-(1,2,4-triazol-1-yl)-ethan-1-ol can be prepared from corresponding cyclopropyl derivatives and used for combating fungi. The activity of these substances is good, but in some cases leaves something to be desired at low application rates.

Novel fluorocyclopropyl derivatives of the formula

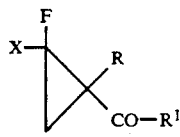

(I)

in which
R represents alkyl, optionally substituted aryl or optionally substituted aralkyl,
X represents hydrogen, chlorine or bromine and
$R^1$ represents hydroxyl, alkoxy, alkyl or halogen,
have now been found.

Furthermore, it has been found that fluorocyclopropyl derivatives of the formula (I) can be prepared by a process in which a) vinyl-cyclopropane derivatives of the formula

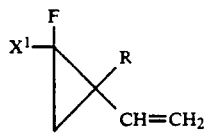

(II)

in which
R has the abovementioned meaning and
$X^1$ represents chlorine or bromine, are reacted with strong oxidants in the presence of a diluent, or b) fluorocyclopropyl derivatives of the formula

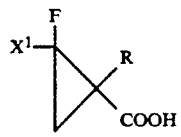

in which
R and $X^1$ have the abovementioned meanings, are reacted either
α) with a halogenating agent, if appropriate in the presence of a diluent, or
β) with alcohols of the formula $$R^2-OH$$ (III)

in which
$R^2$ represents alkyl,
if appropriate in the presence of a catalyst and
if appropriate in the presence of a diluent, or
γ) with hydrogen in the presence of a catalyst and in the presence of an amine and in the presence of a diluent, or c) fluorocyclopropyl derivatives of the formula

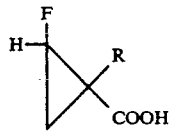

in which
R has the abovementioned meaning, is reacted with a halogenating agent, if appropriate in the presence of a diluent, or d) fluorocyclopropyl derivatives of the formula

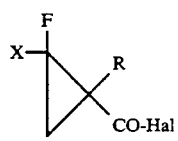

in which
R and X have the abovementioned meanings and
Hal represents halogen, are reacted with alcohols of the formula $$R^2-OH$$ (III)

in which
$R^2$ has the abovementioned meaning,
if appropriate in the presence of a catalyst and
if appropriate in the presence of a diluent, or e) fluorocyclopropyl derivatives of the formula

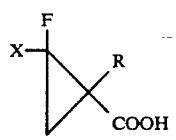

in which
R and X have the abovementioned meanings, are reacted with organometal compounds of the formula $$R^3-Li$$ (IV)

in which
$R^3$ represents alkyl,
in the presence of a diluent.

Finally, it has been found that the novel fluorocyclopropyl derivatives of the formula (I) are very suitable for use as intermediates for the preparation of fluorocyclopropylhydroxyethyl-azoles having fungicidal activity.

Surprisingly, the fluorocyclopropyl-hydroxyethylazoles which can be prepared from the fluorocyclopropyl derivatives of the formula (I) according to the invention show a better fungicidal activity than 1-(4-chlorophenoxy)-2-cyclopropyl-3-(1,2,4-triazol-1-yl)-propan-2-ol and 1-(4-chlorophenyl)-1-(1-chloro-cycloprop-1-yl)-2-(1,2,4-triazol-1-yl)-ethan-1-ol, which are previously known active compounds of a similar structure and a similar direction of action.

Formula (I) provides a general definition of the fluorocyclopropyl derivatives according to the invention.

Preferred compounds are those in which

R represents alkyl having 1 to 4 carbon atoms or represents phenyl which can be monosubstituted to trisubstituted by identical or different substituents from the series comprising halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkylthio having 1 or 2 carbon atoms and 1 to 5 identical or different halogen atoms, alkoximinoalkyl having 1 to 4 carbon atoms in the alkyl moiety and 1 to 4 carbon atoms in the alkoxy moiety, phenoximinoalkyl which has 1 to 4 carbon atoms in the alkyl moiety and which is optionally substituted by alkyl having 1 or 2 carbon atoms and/or halogen, by phenyl which is optionally substituted by alkyl having 1 or 2 carbon atoms and/or halogen, and/or by phenoxy which is optionally substituted by alkyl having 1 or 2 carbon atoms and/or halogen, or R represents benzyl which can be monosubstituted to trisubstituted in the phenyl moiety by identical or different substituents from the series comprising halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, alkoximinoalkyl having 1 to 4 carbon atoms in the alkyl moiety and 1 to 4 carbon atoms in the alkoxy moiety, phenoximinoalkyl which has 1 to 4 carbon atoms in the alkyl moiety and which is optionally substituted by alkyl having 1 or 2 carbon atoms and/or halogen, phenyl which is optionally substituted by alkyl having 1 or 2 carbon atoms and/or halogen, or by phenoxy which is optionally substituted by alkyl having 1 or 2 carbon atoms and/or halogen, X represents hydrogen, chlorine or bromine and $R^1$ represents hydroxyl, alkoxy having 1 to 6 carbon atoms, alkyl having 1 to 6 carbon atoms, fluorine, chlorine, bromine or iodine.

Particularly preferred fluorocyclopropyl derivatives of the formula (I) are those in which R represents methyl, ethyl, isopropyl or tert.-butyl, or represents phenyl which is optionally monosubstituted or disubstituted by identical or different substituents from the series comprising fluorine, chlorine or methyl, or represents benzyl which can be monosubstituted or disubstituted in the phenyl moiety by identical or different substituents from the series comprising fluorine, chlorine and/or methyl, X represents hydrogen, chlorine or bromine and $R^1$ represents hydroxyl, alkoxy having 1 to 4 carbon atoms, alkyl having 1 to 4 carbon atoms, fluorine, chlorine, bromine or iodine.

Very particularly preferred fluorocyclopropyl derivatives of the formula (I) are those in which R represents methyl, ethyl, benzyl or phenyl which is optionally monosubstituted or disubstituted by fluorine, chlorine and/or methyl, X represents hydrogen, chlorine or bromine and $R^1$ represents hydroxyl, methoxy, ethoxy, isopropoxy, n-butoxy, methyl, ethyl, chlorine, bromine or iodine.

If 2-fluoro-2-chloro-1-methyl-1-vinyl-cyclopropane is used as starting substance and potassium permanganate as oxidant, the course 9f process (a) according to the invention can be illustrated by the following equation:

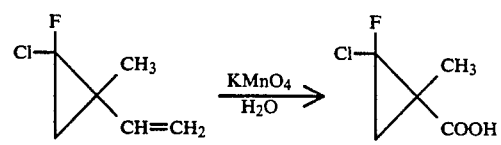

If 2-fluoro-2-chloro-1-methyl-cyclopropane-carboxylic acid is used as starting substance and thionyl chloride as halogenating agent, the course of process (b, variant α) according to the invention can be illustrated by the following equation:

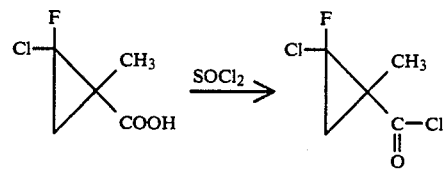

If 2-fluoro-2-chloro-1-methyl-cyclopropanecarboxylic acid and ethanol are used as starting substances and sulphuric acid is used as the catalyst, the course of process (b, variant β) according to the invention can be illustrated by the following equation:

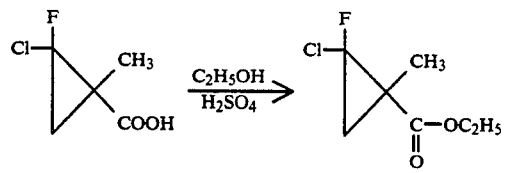

If 2-fluoro-2-chloro-1-methyl-cyclopropane-carboxylic acid is used as starting substance and hydrogen in the presence of Raney nickel and also 1,2-diamino-ethane are used as reactants, the course of process (b, variant γ) according to the invention can be illustrated by the following equation:

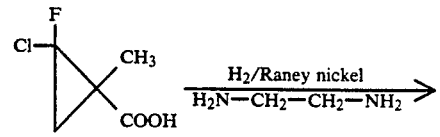

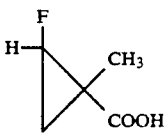

If 2-fluoro-1-methyl-cyclopropane-carboxylic acid is used as starting substance and thionyl chloride as halogenating agent, the course of process (c) according to the invention can be illustrated by the following equation:

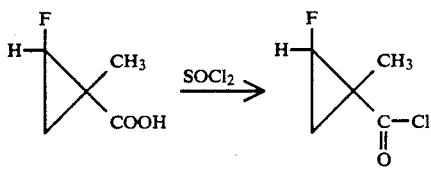

If 2-fluoro-1-methyl-cyclopropane-carbonyl chloride is used as starting substance and ethanol as reactant, the course of process (d) according to the invention can be illustrated by the following equation:

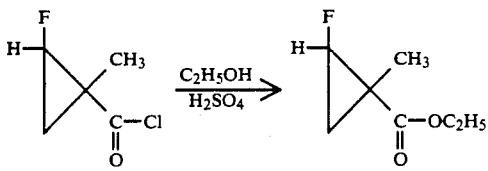

If 2-fluoro-2-chloro-1-methyl-cyclopropanecarboxylic acid is used as starting substance and methyl-lithium as organometal compound, the course of process (e) according to the invention can be illustrated by the following equation:

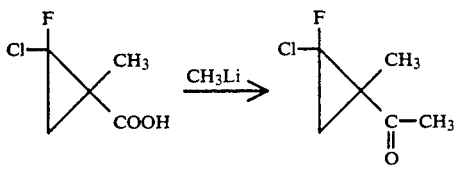

Formula (II) provides a general definition of the vinylcyclopropane derivatives required as starting substances for carrying out process (a) according to the invention. In this formula, R preferably stands for those radicals which have already been mentioned in connection with the description of the substances of the formula (I) according to the invention as being preferred for R. $X^1$ represents chlorine or bromine.

The vinylcyclopropane derivatives of the formula (II) are known or can be prepared by processes which are known in principle (cf. Liebigs Ann. Chem. 710, 17–35 (1967)).

Suitable strong oxidants for carrying out process (a) according to the invention are all those oxidants which are suitable for cleaving olefinic double bonds. Potassium permanganate can preferably be used.

Possible diluents for carrying out process (a) according to the invention are all solvents which are customary for reactions of this type. Water can preferably be used.

When carrying out process (a) according to the invention, the temperatures can be varied within a certain range. In general, the process is carried out at temperatures between 0° C. and 60° C., preferably between 10° C. and 50° C.

Process (a) according to the invention is generally carried out under atmospheric pressure, and so are the other processes described in this application. However, it is also possible in each case to carry out the process under increased or reduced pressure.

When carrying out process (a) according to the invention, 2 to 3 moles of strong oxidant are generally employed per mole of vinylcyclopropane derivative of the formula (II). Working up is carried out by customary methods.

Formula (Ia) provides a general definition of the fluorocyclopropyl derivatives required as starting substances for carrying out process (b) according to the invention. In this formula, R preferably has those meanings which have already been mentioned in connection with the description of the substances of the formula (I) according to the invention as being preferred for this radical. $X^1$ represents chlorine or bromine.

The fluorocyclopropyl derivatives of the formula (Ia) can be prepared by process (a) according to the invention.

Possible halogenating agents for carrying out process (b, variant α) according to the invention are all those substances which are suitable for converting acids into acid halides. Thionyl chloride, sulphuryl chloride, phosphorus trichloride, thionyl bromide and sulphuryl bromide can preferably be used. The acid fluorides and acid iodides can be prepared from the corresponding bromides or chlorides by customary methods.

Suitable diluents for carrying out process (b, variant α) according to the invention are all inert organic solvents which are customary for reactions of this type. It is preferred to use the particular halogenating agent simultaneously as diluent.

When carrying out process (b, variant α) according to the invention, the reaction temperatures can be varied within a relatively wide range. In general, the process is carried out at temperatures between 0° C. and 150° C., preferably between 20° C. and 80° C.

When carrying out process (b, variant α) according to the invention, 1 to 2 equivalents or even a relatively large excess of halogenating agent are employed per mole of fluorocyclopropyl derivative of the formula (Ia). Working up is carried out by customary methods. In order to prepare acid-iodides, acid bromides are reacted with potassium iodide; while acid fluorides are accessible from other acid halides by reacting them with fluorides, such as, for example, sodium fluoride, potassium fluoride, caesium fluoride or ammonium fluoride, or with hydrofluoric acid.

Formula (III) provides a general definition of the alcohols required as reactants for carrying out process (b, variant β) according to the invention. In this formula, $R^2$ preferably stands for alkyl having 1 to 6 carbon atoms.

The alcohols of the formula (III) are generally known compounds of organic chemistry.

Possible catalysts for carrying out process (b, variant β) according to the invention are all reaction enhancers which are customary for the preparation of esters from acids or acid halides. Inorganic acids, such as sulphuric acid, or also strong organic acids, such as p-toluenesulphonic acid, can preferably be used. Inorganic bases, such as sodium hydrogen carbonate or sodium hydroxide, or organic bases, such as pyridine or tertiary amines, can likewise be used.

Suitable diluents for carrying out process (b, variant β) according to the invention are all organic solvents which are customary for reactions of this type. Preferably, alcohol of the formula (III) is employed in excess and act simultaneously as diluent.

When carrying out process (b, variant β) according to the invention, the reaction temperatures can be varied within a relatively wide range. In general, the process is carried out at temperatures between 0° C. and 150° C., preferably between 20° C. and 140° C.

When carrying out process (b, variant β) according to the invention, 1 to 3 moles or even a relatively large excess of alcohol of the formula (III) and a catalytic amount of reaction enhancer are preferably employed per mole of fluorocyclopropyl derivative of the formula (Ia). Working up is carried out by customary methods.

Possible catalysts for carrying out process (b, variant γ) according to the invention are all reaction enhancers which are customary for hydrogenations of this type. Metal catalysts, such as Raney nickel, can preferably be used.

Suitable amines for carrying out process (b, variant γ) according to the invention are all amines which are customary for reactions of this type. 1,2-Diaminoethane can preferably be used.

Possible diluents for carrying out process (b, variant γ) according to the invention are all organic solvents which are customary for reactions of this type. Alcohols, such as methanol or ethanol, and furthermore ethers, such as diethyl ether, dioxane or tetrahydrofuran, can preferably be used.

Process (b, variant γ) according to the invention is generally carried out under a hydrogen pressure between 5 and 30 bar, preferably between 10 and 25 bar.

When carrying out process (b, variant γ) according to the invention, the reaction temperatures can be varied within a relatively wide range. In general, the process is carried out at temperatures between 20° C. and 120° C., preferably between 40° C. and 100° C.

When carrying out process (b, variant γ) according to the invention, 2 to 4 moles of amine and the specifically required amount of catalyst are generally employed per mole of fluorocyclopropyl derivative of the formula (Ia), and hydrogenation is carried out over several hours under increased pressure, using hydrogen. Working up is carried out by customary methods.

Formula (Ib) provides a general definition of the fluorocyclopropyl derivatives required as starting substances while carrying out process (c) according to the invention. In this formula, R preferably has those meanings which have already been mentioned in connection with the description of the substances of the formula (I) according to the invention as being preferred for this radical.

Fluorocyclopropyl derivatives of the formula (Ib) can be prepared by process (b, variant γ) according to the invention.

Suitable halogenating agents for carrying out process (c) according to the invention are all those substances which have already been mentioned as halogenating agents in connection with the description of process (b, variant α) according to the invention.

Apart from this, the reaction conditions for carrying out process (c) according to the invention correspond exactly to those which have been mentioned in process (b, variant α) according to the invention.

Formula (Ic) provides a general definition of the fluorocyclopropyl derivatives required as starting substances for carrying out process (d) according to the invention. In this formula, R preferably has those meanings which have already been mentioned in connection with the description of the substances of the formula (I) according to the invention as being preferred for the radical R. Hal preferably stands for fluorine, chlorine or bromine, and X stands for hydrogen, chlorine or bromine.

The fluorocyclopropyl derivatives of the formula (Ic) can be prepared by processes (b, variant α) and (c) according to the invention.

Suitable alcohols or catalysts for carrying out process (d) according to the invention are all those substances which have already been mentioned as alcohols or reaction enhancers in connection with the description of process (b, variant β) according to the invention.

Apart from this, the reaction conditions for carrying out process (d) according to the invention correspond completely to those which have been mentioned in process (b, variant β) according to the invention.

Formula (Id) provides a general definition of the fluorocyclopropyl derivatives required as starting substances for carrying out process (e) according to the invention. In this formula, R and X preferably have those meanings which have already been mentioned in connection with the description of the substances of the formula (I) according to the invention as being preferred for the radicals R and X.

The fluorocyclopropyl derivatives of the formula (Id) can be prepared by processes (a) and (b, variant γ) according to the invention.

Formula (IV) provides a general definition of the organometal compounds required as reactants for carrying out process (e) according to the invention. In this formula, $R^3$ preferably represents alkyl having 1 to 6 carbon atoms.

The organometal compounds of the formula (IV) are generally known compounds of organic chemistry.

Possible diluents for carrying out process (e) according to the invention are all inert organic solvents which are customary for reactions of this type. Ethers, such as diethyl ether, dioxane or tetrahydrofuran, can preferably be used.

When carrying out process (e) according to the invention, the reaction temperatures can be varied within a relatively wide range. In general, the process is carried out at temperatures between −100° C. and +50° C., preferably between −78° C. and +0° C.

Process (e) according to the invention is carried out under protective gas atmosphere, such as, for example, under argon or nitrogen.

When carrying out process (e) according to the invention, 1.5 to 3.0 moles, preferably 2.0 moles, of organometal compound of the formula (IV) are generally employed per mole of fluorocyclopropyl derivative of the formula (Id). Working up is carried out by customary methods. In general, a procedure is followed in which the reaction mixture is transferred to ice and inorganic acid, the organic phase is separated off, the aqueous phase is extracted using an organic solvent which is sparsely miscible with water, and the combined organic phases are dried and distilled.

The fluorocyclopropyl derivatives of the formula (I) according to the invention are suitable as intermediates for the synthesis of plant protection agents, in particular for preparing substances having fungicidal activity.

Thus, for example, fluorocyclopropyl-hydroxyethyl-triazole derivatives of the formula

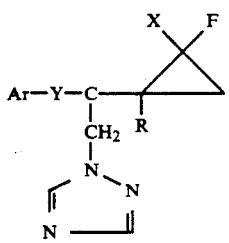 (V)

in which
R and
X have the abovementioned meanings,
Ar represents optionally substituted aryl and
Y represents the groups —OCH$_2$—, —SCH$_2$—, —CH$_2$—CH$_2$— or —CH=CH—,
can be prepared by a process in which
f) methyl-cyclopropyl-ketones of the formula

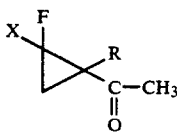 (Ie)

in which
R and X have the abovementioned meanings, are reacted with chlorinating agents or brominating agents, such as sulphuryl chloride, sulphuryl bromide or bromine, in the presence of a diluent, such as methylene chloride, chloroform or carbon tetrachloride, at temperatures between −10° C. and +60° C., preferably between 0° C. and 40° C., and the resulting halogenoketones of the formula

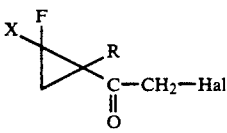 (VI)

in which
R and X have the abovementioned meanings and
Hal represents chlorine or bromine,
are reacted with compounds of the formula

 Ar—Z—H (VII)

in which
Ar has the abovementioned meaning and
Z represents oxygen or sulphur, in the presence of an acid-binding agent and if appropriate in the presence of a diluent at temperatures between 0° C. and 150° C., preferably between 20° C. and 130° C., and the resulting cyclopropyl ketones of the formula

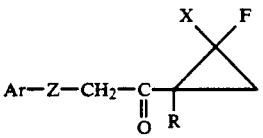 (VIII)

in which
Ar, R, X and Z have the abovementioned meanings, are reacted either

α) with dimethyloxosulphonium methylide of the formula

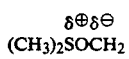 (IX)
(CH$_3$)$_2$SOCH$_2$ or

β) with dimethylsulphonium methylide of the formula

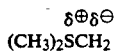 (X)
(CH$_3$)$_2$SCH$_2$ in the presence of a diluent at temperatures between 0° C. and 100° C., preferably between 10° C. and 60° C., and finally the resulting oxiranes of the formula

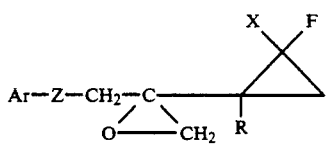 (XI)

in which
Ar, R, X and Z have the abovementioned meanings are reacted with 1,2,4-triazole of the formula

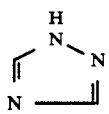 (XII)

in the presence of an acid-binding agent and in the presence of a diluent at temperatures between 0° C. and 200° C., preferably between 50° C. and 150° C., or by a process in which
g) methyl cyclopropyl ketones of the formula

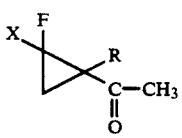 (Ie)

in which
R and X have the abovementioned meanings are reacted with aldehydes of the formula

 Ar—CHO (XIII)

in which
Ar has the abovementioned meaning, in the presence of a catalyst, such as sodium hydroxide or potassium hydroxide, and in the presence of a diluent, such as methanol, ethanol, isopropanol, n-butanol or tert.-butanol, at temperatures between 0° C. and 100° C., preferably between 10° C. and 80° C., and if appropriate the resulting cyclopropyl ketones of the formula

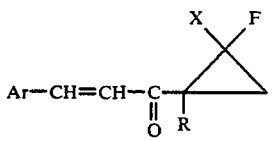
(XIV)

in which
R, X and Ar have the abovementioned meanings, are hydrogenated using hydrogen, in the presence of a hydrogenation catalyst and in the presence of a diluent, and finally the resultant cyclopropyl ketones of the formula

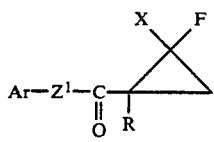
(XV)

in which
Ar, X and R have the abovementioned meanings and $Z^1$ represents the group

—CH$_2$—CH$_2$—, are reacted

α) either with dimethyloxosulphonium methylide of the formula

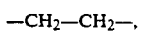
(IX)
(CH$_3$)$_2$SOCH$_2$ or

β) with dimethylsulphonium methylide of the formula

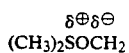
(X)
(CH$_3$)$_2$SCH$_2$ in the presence o& a diluent at temperatures between 0° C. and 100° C., preferably between 10° C. and 60° C., and finally the resulting oxiranes of the formula

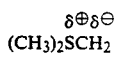
(XVI)

in which
Ar, R, X and $Z^1$ have the abovementioned meanings are reacted with 1,2,4-triazole of the formula

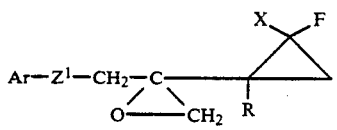
(XII)

in the presence of an acid-binding agent and in the presence of a diluent at temperatures between 0° C. and 200° C., preferably between 50° C. and 150° C.

Furthermore, hydroxyalkinyl-azolyl derivatives of the formula

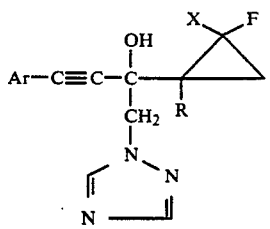
(XVII)

in which
Ar, X and R have the abovementioned meanings, can be prepared in a process in which h) fluorocyclopropyl derivatives of the formula

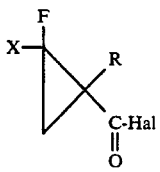
(Ic)

in which
R, X and Hal have the abovementioned meanings, are reacted with acetyl derivatives of the formula Ar—C≡CH     (XVIII)

in which
Ar has the abovementioned meaning, in the presence of a catalyst, such as copper (I) bromide, and in the presence of an acid-binding agent, such as sodium hydroxide or potassium hydroxide, and in the presence of a diluent, such as toluene, at temperatures between 0° C. and 150° C., preferably between 20° C. and 120° C., and the resulting cyclopropyl ketones of the formula

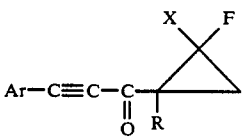
(XIX)

in which
Ar, X and R have the abovementioned meanings, are reacted

α) with dimethylsulphonium methylide of the formula

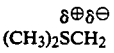
(X)
(CH$_3$)$_2$SCH$_2$ in the presence of a diluent al temperatures between 0° C. and 100° C., preferably between 10° C. and 60° C., and finally the resulting oxiranes of the formula

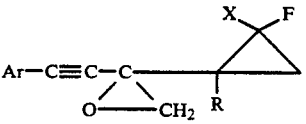
(XX)

in which
Ar, X and R have the abovementioned meanings, are reacted with 1,2,4-triazole of the formula

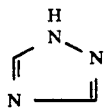 (XII)

in the presence of an acid-binding agent and in the presence of a diluent at temperatures between 0° C. and 200° C., preferably between 50° C. and 150° C.

The remaining fluorocyclopropyl derivatives of the formula (I) can be used in a corresponding manner as intermediates for the synthesis of plant protection agents, in particular substances having fungicidal activity.

The fluorocyclopropyl-hydroxyethyl-triazoles of the formula (V) and the hydroxalkinyl-azolyl derivatives of the formula (XVII) exhibit a powerful microbicidal action and can be employed as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as, for example, *Xanthomonas oryzae*; Pseudomonas species, such as, for example, *Pseudomonas lachrymans*; Erwinia species, such as, for example, *Erwinia amylovora*; Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds of the formulae (V) and (XVII) at the concentrations required for combating plant diseases, permits treatment of above-ground parts of plants, of vegetative propagation stock and seeds, and of the soil.

The active compounds of the formulae (V) and (XVII) are particularly suitable for combating cereal diseases, such as *Erysiphe graminis, Puccinia recondita, Cochliobolus satirus, Pyrenophora teres, Leptosphaeria nodorum* and mildew of barley; furthermore rice diseases, such as *Pyricularia oryzae* and *Pellicularia sasakii* and Venturia species and mildew of cucumber. Moreover, the substances have a very good in-vitro action.

The active compounds of the formulae (V) and (XVII) can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products. As dispersing agents there are suitable: for example ligninsulphite waste liquors and methylcellulose.

Adhesives such as carboxymethylcellulose, natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds of the formulae (V) and (XVII) can be present in the formulations as a mixture with other known active compounds, such as fungicides, insecticides, acaricides and herbicides, as well as in mixtures with fertilizers and growth regulators.

The active compounds of the formulae (V) and (XVII) can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

Depending on the type of application the amount of active compounds of the formulae (V) and (XVII) can be varied within a substantial range. In the treatment of parts of plants, the active compound concentrations in the use forms are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The preparation of the 2,2-difluorocyclopropyl derivatives of the formula (I) according to the invention can be seen from the following examples.

PREPARATION EXAMPLES

Example 1

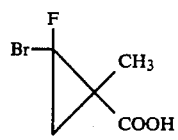
(I-1)

474 g (3 mols) of potassium permanganate are added in portions to 122.5 g (0.91 mol) of 2-fluoro-2-chloro-1-methyl-1-vinyl-cyclopropane in 10 l of water. The mixture is stirred for 36 hours at room temperature and manganese dioxide is filtered off and washed thoroughly with water. The filtrate is acidified using concentrated hydrochloric acid and extracted using dichloromethane. After the organic phase has been dried, the solvent is removed under reduced pressure and the residue is distilled.

In this manner, 115 g (82% of theory) of 2-fluoro-2-chloro-1-methylcyclopropanecarboxylic acid of boiling point 77°–78° C./0.1 mbar are obtained.

Example 2

The compound of the formula

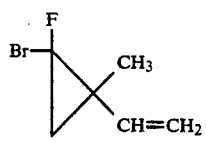
(I-2)

is also obtained following the method indicated in Example 1.

Boiling point: 45°–50° C./0.01 mbar

Preparation of the Starting Substance of the Formula

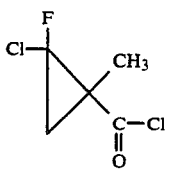
(II-1)

20 ml of 50% strength aqueous sodium hydroxide solution are added dropwise to a vigorously stirred mixture of 7.5 g (0.11 mol) of isoprene, 19 g (0.1 mol) of fluoro-dibromo-methane, 0.5 g (4 mmol) of tetrabutylammonium bromide and 10 ml of dichloromethane such that the reaction mixture boils under vigorous reflux. When the addition is complete, stirring is continued for 5 hours at room temperature, the reaction mixture is then poured into water and extracted several times using diethyl ether, and the combined organic phases are washed with dilute aqueous hydrochloric acid and dilute aqueous sodium hydrogen carbonate solution in succession. After the mixture has been dried it is distilled under reduced pressure. In this manner, 13.2 g (74% of theory) of 2-fluoro-2-bromo-1-methyl-1-vinyl-cyclopropane (cis/trans mixture approx. 1:1) are obtained in the form of a liquid of boiling point 28°–32° C. at 0.01 mbar.

Example 3

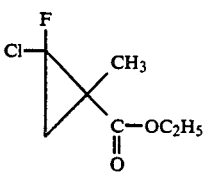
(I-3)

In a distillation equipment, a mixture of 51 g (0.33 mol) of 2-fluoro-2-chloro-1-methylcyclopropanecarboxylic acid and 60 g (0.5 mol) of thionyl chloride is heated slowly with stirring, during which process excess thionyl chloride distils over first and the desired product later. In this manner, 54 g (97% of theory) of 2-fluoro-2-chloro-1-methylcyclopropanecarbonyl chloride are obtained in the form of a liquid of boiling point 82°–85° C./100 mbar.

Example 4

(I-4)

44 ml of ethanol are added at room temperature and with stirring to 43 g (0.28 mol) of 2-fluoro-2-chloro-1-methyl-cyclopropanecarboxylic acid. After the addition of sulphuric acid, the reaction mixture is refluxed for 16 hours. Excess ethanol is subsequently distilled off and the residue is dried and distilled under reduced pressure. In this manner, 40 g (79% of theory) of ethyl 2-fluoro-2-chloro-1-methyl-cyclopropane-carboxylate are obtained in the form of a liquid of boiling point 62°-63° C./17 mbar.

Example 5

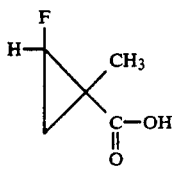
(I-5)

38 g (0.25 mol) of 2-fluoro-2-chloro-1-methylcyclopropanecarboxylic acid (cis/trans mixture) and 30 g (0.5 mol) of 1,2-diaminoethane are dissolved in 750 ml of ethanol. After the addition of 10 g of Raney nickel, the mixture is hydrogenated at 80° C. for 8 hours under a hydrogen pressure of 20 bar. The catalyst is filtered off and the filtrate is washed with dilute aqueous hydrochloric acid and with water in succession, then dried and distilled. In this manner, 21 g (71 % of theory) of 2-fluoro-1-methylcyclopropane-carboxylic acid (cis/-trans mixture) are obtained in the form of a liquid of boiling point 52°-54° C. at 0.1 mbar.

Example 6

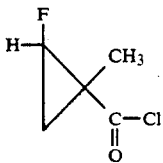
(I-6)

In a distillation equipment, a mixture of 51 g (0.43 mol) of 2-fluoro-1-methyl-cyclopropane-carboxylic acid (cis/trans mixture) and 100 ml of thionyl chloride is slowly heated with stirring, during which process excess thionyl chloride distils over first and the desired product later. In this manner, 56 g (93% of theory) of 2-fluoro-1-methyl-cyclopropane-carbonyl chloride (cis/-trans mixture) are obtained in the form of a liquid of boiling point 40°-42° C. at 20 mbar.

Example 7

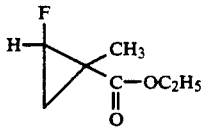
(I-7)

40 ml of ethanol are added dropwise at 20° C. and with stirring to 20 g (0.12 mol) of 2-fluoro-1-methyl-cyclopropane-carbonyl chloride (cis/trans mixture). After the addition of 2 drops of concentrated sulphuric acid, the reaction mixture is refluxed for one hour. Excess ethanol is subsequently distilled off, and the residue is dried and distilled under reduced pressure. In this manner, 18.4 g (85% of theory) of ethyl 2-fluoro-1-methyl-cyclopropanecarboxylate (cis/trans mixture) are obtained in the form of a liquid of boiling point 42°-45° C. at 18 mbar.

$n_D^{20} = 1.4069$.

It is understood that the specification and examples are illustrative but not limitative of the present invention and that other embodiments within the spirit and scope of the invention will suggest themselves to those skilled in the art.

We claim:

1. A fluorocyclopropyl derivative of the formula

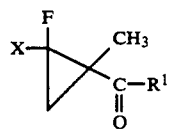

in which

X represents hydrogen, chlorine or bromine and
$R^1$ represents hydroxyl, methoxy or ethoxy.

2. A compound according to claim 1, wherein such compound is 2-fluoro-2-chloro-1-methylcyclopropanecarboxylic acid of the formula

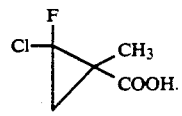
(I-1)

3. A compound according to claim 1, wherein such compound is 2-fluoro-2-bromo-1-methylcyclopropanecarboxylic acid of the formula

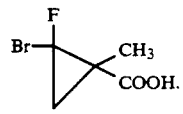
(I-2)

4. A compound according to claim 1, wherein such compound is ethyl 2-fluoro-2-chloro-1-methyl-cyclopropanecarboxylate of the formula

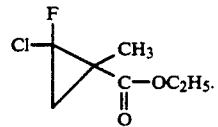
(I-4)

5. A compound according to claim 1, wherein such compound is 2-fluoro-1-methyl-cyclopropane-carboxylic acid of the formula

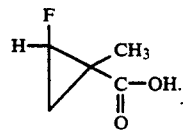
(I-5)

* * * * *